United States Patent [19]
Larsson

[11] Patent Number: 4,857,051
[45] Date of Patent: Aug. 15, 1989

[54] BREASTPUMP

[75] Inventor: Karl O. A. H. Larsson, Zug, Switzerland

[73] Assignee: ISG/AG, Zug, Switzerland

[21] Appl. No.: 53,055

[22] Filed: May 22, 1987

Related U.S. Application Data

[63] Continuation-in-part of Ser. No. 874,879, Jun. 6, 1986, abandoned, which is a continuation of Ser. No. 612,602, May 21, 1986, abandoned, which is a continuation-in-part of Ser. No. 296,081, Aug. 25, 1981, abandoned.

[30] Foreign Application Priority Data

Sep. 5, 1980 [CH] Switzerland ............ 6706/80
May 20, 1983 [CH] Switzerland ............ 2782/83

[51] Int. Cl.$^4$ ............................................. A61M 1/06
[52] U.S. Cl. ........................................ 604/74; 604/346
[58] Field of Search ............................ 604/74–76, 604/118, 119, 323, 335, 346; 119/14.32, 14.33, 14.53; 137/533.19

[56] References Cited

U.S. PATENT DOCUMENTS

| | | | |
|---|---|---|---|
| 1,184,293 | 5/1916 | Zeratsky | 119/33 |
| 3,583,434 | 6/1971 | Muller | 137/533.19 |
| 3,977,405 | 8/1976 | Yanase | 604/74 |
| 4,573,969 | 3/1986 | Schlensog et al. | 604/74 |
| 4,673,388 | 6/1987 | Schlensog et al. | 604/74 |

FOREIGN PATENT DOCUMENTS

| | | | |
|---|---|---|---|
| 395101 | 5/1924 | Fed. Rep. of Germany | 604/74 |
| 407293 | 9/1944 | Italy | |
| 762701 | 12/1956 | United Kingdom | 604/74 |

*Primary Examiner*—Jerome L. Kruter
*Attorney, Agent, or Firm*—Willian Brinks Olds Hofer Gilson & Lione Ltd.

[57] ABSTRACT

A breastpump is provided with a valve mechanism that closes a collection chamber when a vacuum is applied to a hood member and opens the collection chamber when the vacuum is removed. The valve mechanism is removably attached to the collection chamber for ready cleaning. A baffle in the hood member protects the vacuum line from milk flow. One embodiment of the invention has a connecting sleeve for connecting either a manually driven pneumatic pump or a motor driven pneumatic pump to the hood body to create an intermittent vacuum. A connector is further provided for use with a pair of breastpumps operated simultaneously by a motor driven pneumatic pump. An adjustment piece for decreasing the cross-sectional area of a funnel-shaped hood member is also disclosed for use of the breastpumps with smaller breasts. One type of manually driven piston pump useful with the invention has apertures formed through the pump cylinder wall that are selectively opened and closed for adjustment of the piston pump vacuum.

5 Claims, 4 Drawing Sheets

FIG-2

FIG_2A_

4,857,051

BREASTPUMP

This is a continuation-in-part application of U.S. patent application Ser. No. 874,879 filed June 6, 1986 now abandoned, which is a continuation of Ser. No. 612,602 filed May 21, 1984 (now abandoned), which is a continuation-in-part of Ser. No. 296,081 filed Aug. 25, 1981 (now abandoned).

FIELD OF THE INVENTION

The present invention generally relates to breastmilk pumps, and more particularly relates to a new and improved: valving mechanism for a breastmilk pump; a suction hood for a breastmilk pump; a manually adjustable pump-vacuum control mechanism for a manual pump; and an adaptor for pumping milk from two breasts simultaneously.

BACKGROUND OF THE INVENTION

Breastmilk pumps are well known, and are generally comprised of a hood that fits over the breast, a vacuum pump connected to the hood for generating an intermittent vacuum within the hood, and a receptacle for the expressed milk. Manually driven vacuum pumps as well as those that are driven by a motor are ordinarily used. The vacuum pumps of these devices, as a rule, intermittently generate a vacuum or negative pressure within the hood, with the hood encompassing the nipple and a substantial amount of the breast. The intermittent suction action of the pumps serves to pull on the breast and thereby extract milk in an action reminiscent of suckling. The milk so extracted typically flows from the hood into a collection container for storage and later use.

Apart from the purely hygienic requirements for such equipment, there also exist technical problems which are at least insufficiently solved with regard to prior art devices. One such significant failing of nearly all of the prior art devices is that the milk expressed often reaches the vacuum line or even the pump. In order to eliminate such a serious problem, many prior devices contain so-called safety volumes between the hood and the pump. Such a solution of the problem is expensive and usually cannot provide effective protection of the vacuum line and pump from milk. Also, varying degrees of vacuum can be generated as the milk receptacle fills, which must then be compensated for.

Another important consideration in the design of a breastpump is the vacuum created by the pump and its effect upon the breast. While it is the ultimate desire to design a breastpump that perfectly duplicates a baby's nursing action, this is extremely difficult to achieve. However, there are several important characteristics that a breastpump, properly designed, can simulate. Three things about the vacuum and its application to the breast are considered very important. These are: (a) how much vacuum does a pump create on the breast; (b) how long is that vacuum applied to the breast; and (c) can the vacuum be regulated within safe, natural limits to suit the mother's comfort with proper expression of milk?

First, a vacuum that is much greater than that "vacuum" created by a suckling baby is not only unnatural, it can also cause pain and injury to the breast. Second, just as too much vacuum can hurt the breast, too long an application of vacuum is also unnatural, and may create discomfort and injury. Third, uncontrollable vacuum—either vacuum in excess of safe, natural limits or vacuum that cannot be finetuned for a woman's comfort—makes a breastpump less effective or even useless.

In utilizing breastpumps, whether they are of a motor driven or manually driven type, it has been found that the wide variety in the size of breasts also gives rise to problems if a single breastpump is to be given universal application. This is particularly true in regard to smaller breasts, since the hoods used by most breastpumps are designed to handle a medium or larger-size breast. For example, the small breast can be sucked into a standard size hood to an extent that, if not necessarily painful, is at least rather uncomfortable. In general, the funnel of such a suction hood should abut the breast at a distance from the nipple that is as large as possible, which condition demands a funnel for the hood which is also as large as possible. While it has become obvious that the provision of different suction hoods having various funnel diameters solves such a problem, it does so in an unsatisfactory way, since providing a product line of different size hoods is expensive from a marketing and manufacturing standpoint.

SUMMARY OF THE INVENTION

One of the principal objects of the present invention is to provide a breastpump that has an improved structure including a simple but effective valving mechanism which prevents breastmilk from entering the vacuum line or suction pump.

A particularly noteworthy advantage of the valving mechanism of the present invention is that a relatively constant negative pressure or vacuum can be applied to the breastpump, since no variable volumes, (i.e., in the receiving container), are present in this device. This allows the employment of smaller pumps, since the volume of the vacuum or negative pressure which is necessary for intermittent operation can be considerably smaller in comparison to other known solutions. It is also not necessary to create a vacuum to compensate for the volume of the receiving container due to the presence of the valve of the present invention.

Another object of the present invention is to provide a breastpump that has a readily adjustable vacuum in a manually driven (non-motor) application.

Yet another object of the present invention is to provide a new and improved construction of a suction hood for a breastpump, which suction hood is relatively simple in construction and design, economical to manufacture, extremely reliable in operation, not readily subject to breakdown or malfunction, and requires a minimum of maintenance and servicing yet is effective in expressing breastmilk without fouling the equipment.

Still another object of the present invention is to provide a breastpump assembly which collects milk from both breasts simultaneously.

To these ends, which will become more readily apparent in regard to the detailed description of various embodiments of the invention which follows, the present invention comprises a hood body or member to which a collecting or catch chamber is connected. At the outlet of the collecting chamber there is provided a valve which closes a passage leading from the collecting chamber to a receiving container. When a vacuum or negative pressure is applied to the hood from a suction device, which may be manually operated or motor driven, the valve closes the collecting chamber outlet to the receiving chamber, but opens the outlet on the return cycle of the pump to force the milk expressed from the collecting chamber into the receiving chamber.

The valve used is extremely effective, simple in construction, and is easily cleaned. In one embodiment the valving mechanism comprises a ball valve. In a second and presently preferred construction, the valving mechanism comprises a reciprocating disk. In this latter construction, the valving mechanism is part of an adaptor that is removably attached to an extension of the hood that forms part of the collecting chamber, so that the valve can be readily removed for cleaning.

It will be noted that due to the provision of the collecting or catch chamber with a valve, milk can be pumped to a receiving container in the form of a plastic bag, since the vacuum or negative pressure no longer affects the receiving container. Moreover, an overflow can be avoided, since the valve opens promptly and the expressed milk quickly flows into the receiving container.

A baffle arrangement is further used in conjunction with the valve mechanism to prevent milk from passing into the vacuum line or from reaching the vacuum pump.

The present invention also provides a breastpump that, in a manual mode (i.e., using a piston pump that is hand operated), applies a governed vacuum to express milk from the breast. With an electric motor driven pneumatic pump, its maximum vacuum and timing are governed by the machine and remains relatively constant. With hand-driven piston pumps, too much vacuum could be applied to the breast and for an undesirably long interval, depending on the speed and length of stroke with which the woman is operating the piston pump. The present invention provides for a vacuum release within the piston cylinder that automatically releases the vacuum as soon as the maximum desired vacuum is reached at the end of a predetermined stroke.

The present invention also provides for the adjustment of the vacuum level in the hand-driven piston pump application of the invention. This is accomplished in a preferred form of the invention through the use of a rotatable ring on the piston cylinder that selectively opens and closes apertures in the cylinder to adjust the flow of air into the cylinder during an evacuation stroke of the piston, and thereby adjust the amount of vacuum generated. The vacuum control is readily manipulated for easy adjustment of the vacuum generated.

The problem of the small breast that does not fit the "standardized" construction of the hood is solved in the present invention by providing an improved construction for the suction hood which includes at least one adjusting piece having a shape similar to that of the general funnel structure of the main funnel of the hood, and which is insertable into the main hood funnel to reduce the latter's cross-sectional area. In particular, a preferred funnel-shaped adjusting piece has a generating angle for the outer surface of the adjusting piece funnel which corresponds to the generating angle of the inner surface of the main funnel of the hood, with the inner surface of the adjusting piece having a larger generating angle than that of the inner surface of the main funnel. The adjusting piece effectively reduces the diameter of the main funnel at the base of the main funnel so that the hood can be conveniently used by women with smaller breasts.

Yet another object of the present invention is accomplished in the use of a device that enables a single motor driven pneumatic pump to express milk from two breasts simultaneously. The device comprises a y-shaped tubular connector that permits use of two of the foregoing breastpumps at the same time.

The foregoing objects and advantages of the present invention will be further understood upon consideration of the following detailed description of the invention taken in conjunction with the accompanying drawings, in which:

DETAILED DESCRIPTION OF EMBODIMENTS OF THE INVENTION

Figures 1, 3:
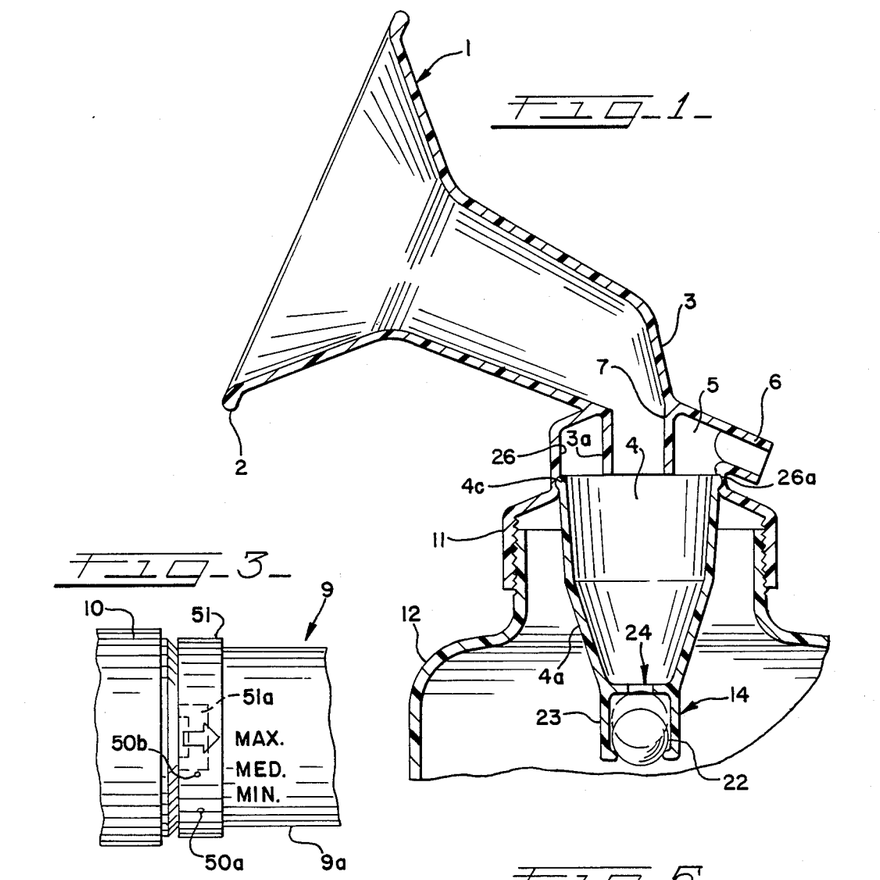
FIG. 1 is a partial vertical sectional view of a first embodiment of a breastpump made in accordance with the present invention in which a ball valve is used.
FIGS. 3 through 5 show a vacuum adjustment mechanism for use with the manually driven suction pump of the device of FIG. 2A.

Turning now to FIG. 1, a first embodiment of a breastpump made in accordance with the teachings of the present invention is shown. This arrangement comprises a hood body or hood member 1 having two ends. The first end 2 has a substantially wide cross-section (diameter), and is funnel shaped. During operation of this device, funnel end 2 is placed over the breast of the user. A second end 3 of the hood member constitutes a generally cylindrical extension of the funnel, and has a cross-section substantially narrower than the cross-section of the end 2. The second end 3 communicates with a collecting or catch chamber 4 and with a vacuum passage 5 via a short tubular extension 3a.

The vacuum passage 5 also communicates with a vacuum line 6, which in this embodiment is shown as a short stem which is connected with a flexible tube (not shown) that extends to a vacuum or suction pump, such as an electric motor driven pneumatic pump.

The collecting chamber 4 is arranged substantially immediately after the extension 3a of the hood. Separating means in the form of a depending separation wall 7 (which here is the rear wall of the extension 3a) forms a baffle between the end of the hood extension 3a and the collecting chamber 4, and the vacuum line 6. It will be noted that the bottom of the separation wall 7 is below the level of the top end of the vacuum line 6. Milk expressed into the hood member 1 is thus blocked by the separation wall 7 from thereby entering into the vacuum line 6.

At the lower portion of the collecting chamber 4 is a valve mechanism 14. In this embodiment, this valve mechanism 14 is a ball-type valve having a ball 22 captured within a cage 23 formed in the bottom of a cup-like receptacle 4a that defines the majority of the collecting chamber 4. The top of the ball valve cage 23 has an upper opening 24 which is opened and closed by action of the ball 22. Opening 24 constitutes the outlet for the collecting chamber 4. In operation, the application of a suction or negative pressure to the hood member 1 and collecting chamber 4 by the suction pump connected to the vacuum line 6 causes the ball 22 to be drawn upwardly (as shown in FIG. 1) to close the upper opening 24. Milk expressed through the suction action will thus collect in the collecting chamber 4. Release of the negative pressure will thereupon cause the ball 22 to drop free of the opening 24 allowing the milk to flow around the ball through the ball valve cage 23 and into a container or receptacle 12.

The collecting receptacle 4a is of a size to allow a typical volume of milk expressed in a single stroke to collect without overflowing, with the action of the ball valve being sufficiently quick to release the milk from the collecting chamber 4 into the container 12 for the next stroke. Milk thus does not substantially collect in the collecting chamber 4 between strokes.

It will be further noted that the collecting chamber receptacle 4a is received in an enlarged portion 26 at the tail-end of the hood member 1. A snap-fit is made using a bead 4c formed around the top edge of the collection chamber receptacle 4a that is received in annular recess 26a. The snap-fit permits easy removal of the collection chamber receptacle 4a and valve mechanism 14 for cleaning, as well as for cleaning of the hood member 1. Also, connecting means in the form of a collar 11 is provided for connection of the hood member 1 and the collecting chamber 4 with the container 12, as through the screw-threaded attachment of the collar 11 to the neck of the container 12.

Figure 2:
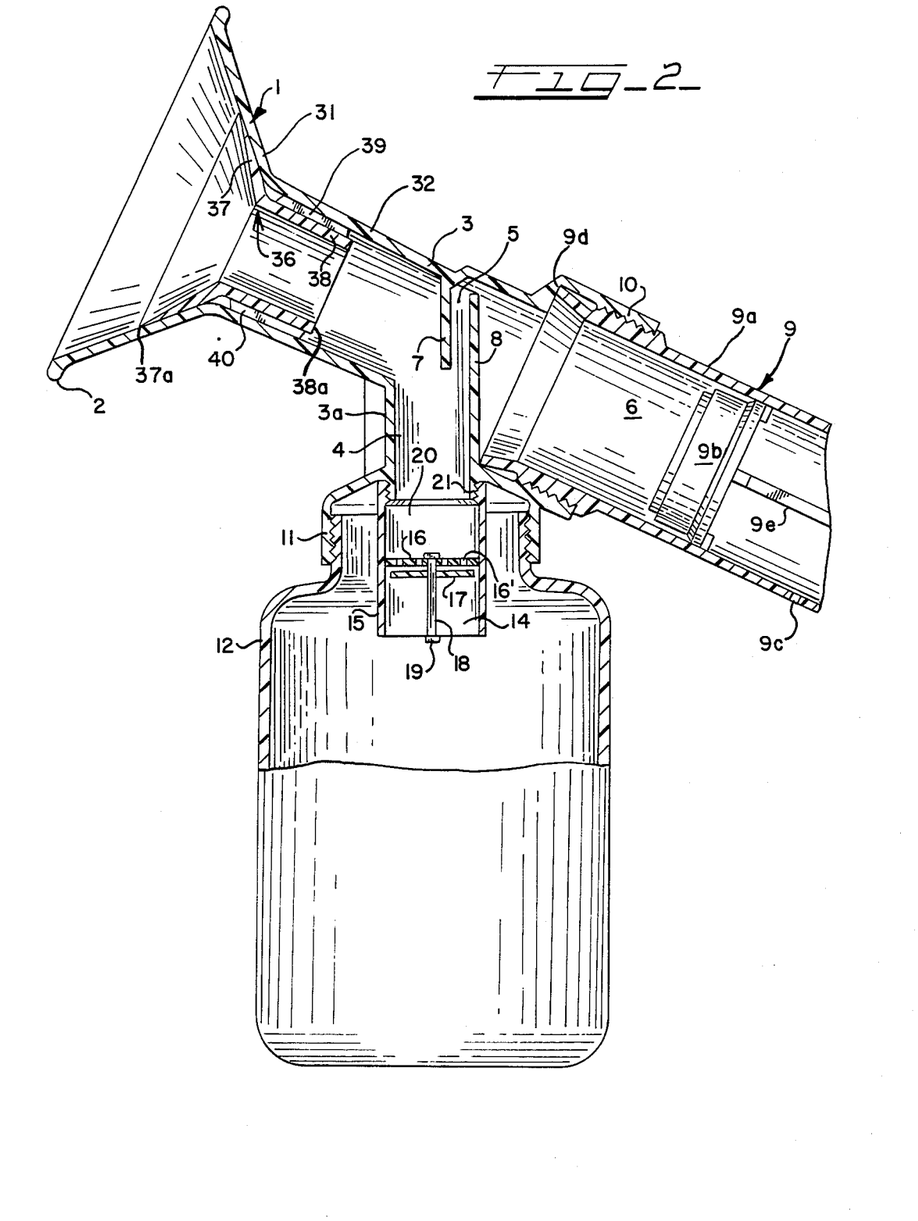
FIG. 2 is a view similar to that of FIG. 1 showing another embodiment of a breastpump made in accordance with the present invention using a manually driven suction pump mechanism, and employing a disk valve mechanism, and shows as well the use of an adaptor for small breasts.

A second possible embodiment of the invention is shown in FIG. 2, and employs a valving mechanism that is different from that of the preceding embodiment, but operates on the same general principle. This valving mechanism shown in FIG. 2 is not presently preferred, with the valving mechanism of FIG. 2A being considered much more advantageous. It will further be understood that like numbers denominate the same general structure of element in all of the various embodiments shown in the FIGS.

In FIG. 2, the suction or vacuum pump is specifically shown as a manually driven piston pump 9 having a pump cylinder 9a and a piston 9b which reciprocates within the cylinder 9a under action of a piston rod 9e. The pump cylinder 9a is connected to the hood member 1 by means of a connecting means or connecting sleeve 10 which forms part of the hood member 1. Connecting sleeve 10 is internally screw threaded to match with the screw threads formed on the outer part of an end of the piston cylinder 9a. Forward end 9d of the piston cylinder butts against a shoulder formed around the interior of the connecting sleeve 10 in a substantially air-tight fit. An aperture 9c is formed in the wall of the piston cylinder 9a at a point which corresponds to what is presently considered to be the maximum desired vacuum pressure to be reached on an average stroke of the manually driven piston pump. Once the head of the piston 9b passes beyond this aperture 9c in its downward (vacuum-inducing) stroke, the vacuum produced is automatically released. The piston cylinder has a displacement (volume at full outward stroke) of about 40 cc at the point of the vacuum release.

The valve 14 in the embodiment of FIG. 2 is of a disk-type valve composed of a tubular housing 15, a perforated plate 16 that extends across the diameter of the housing 15, a disk 17, a guiding member 18 and a stop member 19. The disk 17 is adapted to travel along the guide 18 between a closed and an open position of the valve 14.

The valve 14 includes an upper chamber 20 which forms part of the collecting chamber 4, and collects milk when the valve 14 is in a closed position (with the disk 17 in facial engagement with the bottom of the perforated plate 16, thereby closing the openings 16' of the perforated plate). The tubular housing 15 of valve 14 is removably attached to the hood member 1 by means of a suitable releasable closure attaching means 21. In this embodiment of the invention, this attaching means is accomplished through a threaded engagement with the hood extension 3a.

During the operation of the embodiment of FIG. 2, the hood member 1 is held against the breast of the user with the main funnel body or portion 31 surrounding the nipple and adjacent breast. An intermittent vacuum is created by operation of the pump 9. The vacuum created in the collecting chamber 4 causes the disk 17 to be lifted to an upper position which sealingly closes apertures 16' of the perforated plate 16.

Due to the sealing engagement between an inside portion of the main funnel body 31 of the hood member 1 and the breast during the application of the vacuum, the milk is sucked from the breast of the user. The force of gravity causes the milk to be accumulated in the collecting chamber 4, particularly in the upper portion 20 of the valve housing 15. As soon as the negative pressure is discontinued, the disk 17 drops into its lower position and the milk which has been collected in the collecting chamber 4 thereby flows downwardly into the container 12.

Separation wall 17 combines with a rear wall 8 of the hood member extension 3a to form a baffle to prevent milk from reaching the vacuum line 6. This baffle forms a more restricted vacuum passage 5 than that of FIG. 1 for better protection of the vacuum line 6.

Figure 2A:
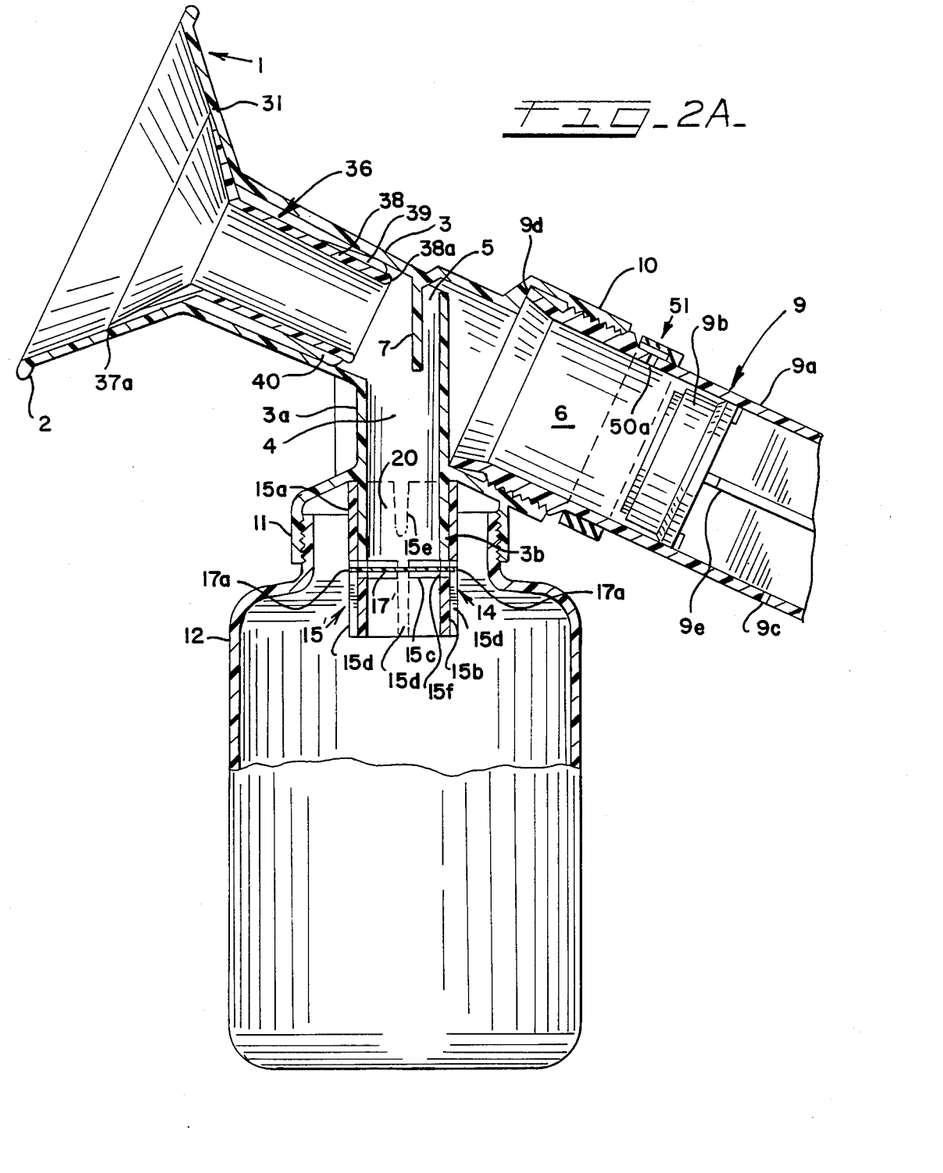
FIG. 2A is a view similar to that of FIG. 2 showing yet another embodiment of a breastpump made in accordance with the present invention.

Yet another embodiment of the invention is depicted in FIG. 2A. This embodiment differs from that of FIG. 2 only in respect of the valve 14 and an insert or adjusting piece 36 which is inserted into the main funnel body 31. This adjustment piece 36 will be discussed in further detail hereafter.

The valve mechanism 14 of FIG. 2A also uses a disk-member 17' as the valve member, but does away with a guiding member such as that illustrated at 18 of FIG. 2. Instead, disk 17' is captured within a tubular shaped valve housing 15' that has an upper portion 15a and a lower portion 15b. Lower portion 15b has a slightly smaller interior diameter than that of the upper portion 15a. A small gap 15c is formed between the upper and lower portions 15a, 15b within which the disk 17' is captured and vertically reciprocates. Ribs 15d connect the top and the bottom portions 15a, 15b. Nibs 17a formed on the disk 17' extend beyond the inboard edge of the top portion 15a to further locate the disk member 17' within the gap 15c. These nibs 17a abut against the bottom edge of the upper housing portion 15a when the housing 15' is removed from the hood member 1.

When the vacuum pump 9 is operated with the embodiment of FIG. 2A, the disk 17' is caused to move upwardly under vacuum where it contacts and seats against the bottom edge or lip of an extended length 3b of tubular extension 3a, thus closing the upper portion 20 of the housing 15' and thereby closing the collecting chamber 4. When the vacuum is released, the disk 17' drops from the foregoing seat and rests upon stand-off bosses 15f formed on the top of the lower housing portion 15b. This allows the milk collected in the upper housing portion 20 and collecting chamber 4 to flow downwardly into the container 12.

As in the embodiment of FIG. 2, the valve 14 of this embodiment is also releasably attached to the end of the hood member 1. That attachment takes the form of a split-collar arrangement for the upper housing portion 15a, as shown by the slot 15e formed in the upper portion 15a. The internal diameter of the upper portion 15a is slightly smaller than the outside diameter of the lengthened portion 3b of extension 3a of the hood end. The slotted portion 15a can thus be releasably wedged on the lengthened portion 3b.

An adjusting piece 36 is shown in both FIGS. 2 and 2A comprising a funnel-shaped section 37 that is made integral with a cylindrical portion 38 that forms an extension of the funnel section 37. The extension portion 38 abuts against the inner surface of a similar cylindrical portion 32 that forms an extension of the main funnel 31 of the hood member 1 through the use of wing-shaped rib or distance pieces 39, 40. The adjusting piece 36 reduces the diameter of the base of main funnel 31 for use of the breastpump with smaller breasts.

The generating angle of the outer surface of the funnel 37 of the adjusting piece 36 corresponds to the generating angle of the inner surface of the main funnel 31. The generating angle of the inner surface of the adjusting piece funnel 37 is slightly larger, however, and thus decreases the operative cross-section of the main funnel 31. The adjusting piece 36 thus reduces the opening into the extension 32 of the hood member 1. This enables the main funnel 31 to still abut a significant amount of the breast along a large distance from the nipple without a smaller breast being sucked into the extension 38 of the adjusting piece 36.

It will also be noted that the funnel 37 of the adjusting piece 36 terminates in a sharp edge 37a to lie ridgelessly on the inner surface of the main funnel 31. This sharp edge 37a provides a good seal between the adjusting piece funnel 37 and the main funnel 31. This in turn provides a correct seal between the breast and the main funnel 31, the result of which is that no significant amount of air will be sucked by the breastpump during use. This sharp-edge engagement between the adjusting piece funnel 37 and the main funnel 31 also provides a smooth surface within the hood member 1 that prevents irritation of the breast during use of the breastpump.

Extension 38 of the adjusting piece 36 is long enough to accommodate the full length of the compressed nipple therein without the nipple extending significantly beyond an inner end 38a of the adjusting piece. The suction force upon the breast nipple causes the nipple areola to extend radially, with the nipple desirably pressed on the inner surface of the adjusting piece 36 but not beyond the inner end 38a of the extension 38. As shown in FIG. 2, the adjusting piece extension 38 is approximately half as long as the extension 32 of the main funnel 31. Adjusting piece 36 has a slightly longer extension 38 in the embodiment of FIG. 2A.

The present invention also provides for adjustment of the amount of vacuum generated during manual pumping. This feature of the invention is illustrated in FIG. 2A and particularly in FIGS. 3 through 5, which show a modification made to the type of hand-operated piston pump 9 of FIG. 2.

Figure 5:
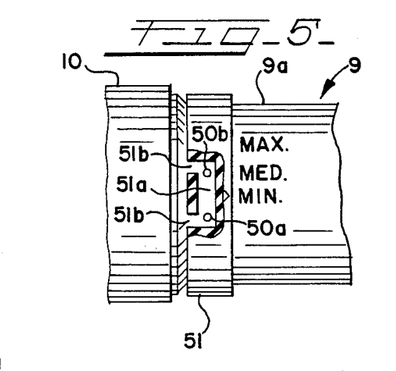

A pair of spaced apart apertures in the form of pin holes 50a and 50b are formed through the pump cylinder 9a adjacent to the end 9d of the piston cylinder. The pin holes 50a, 50b each have a diameter of about 0.6 mm. A ring 51 carried on the piston cylinder 9a overlies the cylinder holes 50a, 50b. An interior chamber or channel 50a is formed on the inside of the ring 51. This interior channel 51a is sufficiently long to allow both of the holes 50a, 50b to fit within the channel 51a simultaneously (FIG. 5). The channel 51a has openings 51b at either end that are open to atmosphere. The ring 51 is preferably made out of a flexible or semi-flexible rubber-like material that grips the outside of the pump cylinder 9a and enables a good seal to be maintained between the ring and the piston cylinder.

Figure 4:
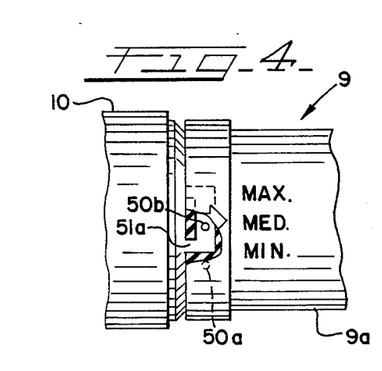

The ring 51 is designed to be rotated on the piston cylinder to positions indicated as "Maximum", "Medium" and "Minimum" vacuum, as illustrated in the FIGS. 3 through 5. Maximum vacuum (FIG. 3) has neither hole 50a or 50b within the area of the channel 51a. The holes 50a, 50b are covered by the ring 51 and no air enters the piston cylinder 9a therethrough.

Medium vacuum is established by rotating the ring 51 so that hole 50b is within the channel 51a. Air can thus enter through the channel openings 51b into the channel 51a and through the hole 50b into the pump cylinder 9a to thereby modify the vacuum (FIG. 4).

Minimum vacuum is established by rotating the ring 51 so that both of the holes 50a, 50b are located within the channel 51a (FIG. 5). The amount of vacuum or pull on the breast generated by the manual pump 9 can thus be readily adjusted by the user as circumstances warrant.

Figures 2B, 6:
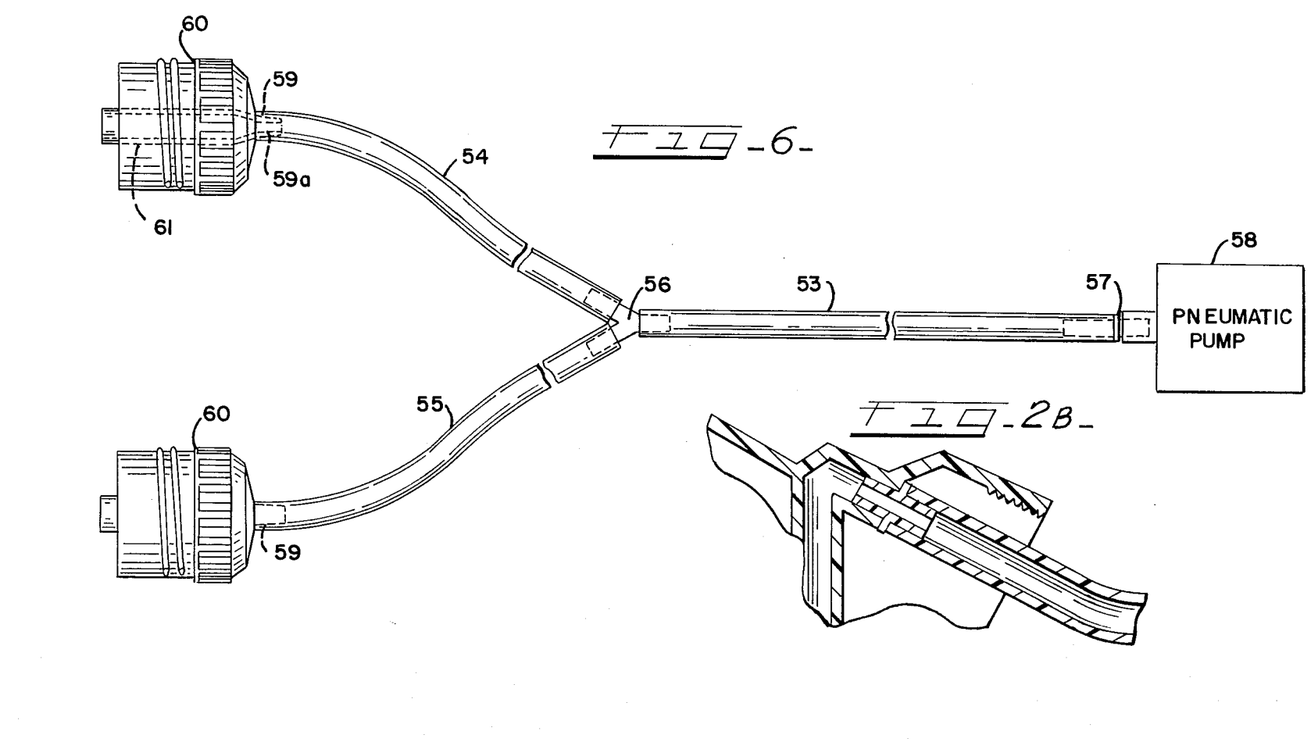
FIG. 2B is an enlarged sectional view of a modified connector for use with a motor driven pump.
FIG. 6 shows a connector for a double-pump application for use in collecting milk from two breasts simultaneously.

Yet another feature of the invention is illustrated in FIG. 6 for operating two breastpumps simultaneously. This is possible when using an electric motor driven pneumatic pump. Two of the breastpumps illustrated in any of FIGS. 1, 2, or 2A could be used in this application. FIG. 6 illustrates a device to be used when expressing milk from both breasts simultaneously that is particularly adapted for use with the breastpumps of FIGS. 2 and 2A, however. This device comprises a Y-shaped connector formed from a flexible base hose or tube 53 and flexible extension hoses or tubes 54 and 55, the latter tubes forming the arms of the Y. A Y-shaped hollow connector piece 56 includes a plurality of attachment stems that the respective tubes 53 through 55 fit over.

One end of the base tube 53 is connected via a hollow connector piece 57 to the output of a suitable motor driven pneumatic pump 58. Ends of the extension tubes 54, 55 fit over nipples 59 formed on a screwthreaded adaptor 60. The nipples 59 have an internal opening 59a which extends into a tubular portion 61 of the adaptor 60. Adapters 60 are specifically designed for use in the embodiments of FIGS. 2 and 2A, and are screw threaded to the sleeve 10 in place of the manually driven pump 9. The embodiments of the breastpump depicted in these two FIGS. can thus be used with a motor driven vacuum pump as well as with a manually driven piston pump.

FIG. 2B illustrates another adaptation for the breast pump of this invention which enables hook-up to a pneumatic pump (such as pump 58). A tubular connector 62 has an end sized to snuggly fit, in an interference fit, within a widened opening 5a to the vacuum channel 5, which is provided with an elbow-type bend to this end. A flange 62a around the middle of the connector 62 serves as a stop within the elbow, and also forms a stop for a tube 63 which is connected to the other end of the connector 62. The tube is connected at its opposite end to a motor driven pump. No adapter, such as adapter 60, is thus necessary with this embodiment using the connector 62.

Thus, while the invention has been described with reference to certain present embodiments, those skilled in this art will recognize modifications of structure, arrangement, composition and the like that can be made to the present invention, yet still fall within the scope of the invention as hereafter claimed.

What is claimed is:

1. A breastpump comprising:
   a hood body for placement over a breast, said hood body having a main funnel-shaped portion within which the breast is received and a tubular extension extending downstream from said main funnel portion;
   means for connecting said tubular extension of said hood body with a vacuum line to periodically withdraw air from said hood body in a manner that draws the breast into said main funnel portion and thereby express milk from the breast into said tubular extension;
   a wall formed interiorly of said tubular extension separating said vacuum line connecting means from the breastmilk flow, said wall depending from an upper interior side wall of said tubular extension with said vacuum line connecting means having a connection with said tubular extension above the bottom of said wall, said wall forming a baffle preventing milk from entering said vacuum line;
   a catch chamber for expressed milk connected with said tubular extension, said catch chamber being located downstream from said tubular extension and having an inlet and an outlet;
   a valve mechanism located at said catch chamber outlet, said valve mechanism having a valve member which closes said catch chamber outlet when a vacuum is applied to said hood body and opens said catch chamber outlet when said vacuum is removed;
   said valve mechanism comprising a tubular valve housing having a circumferential slot formed therethrough dividing said housing into an upper portion and a lower portion, a solid disk-shaped valve member sized larger than said collecting chamber outlet and adapted to seat against a lip defining said outlet when a vacuum is applied to said hood body to thereby close said outlet, said disk-shaped valve member having radially extended nibs which engage an edge formed on the bottom of said upper valve housing portion when said valve mechanism is not attached to said hood body, with ribs extended between said upper and lower valve housing portions joining said upper and lower housing portions without substantially obstructing said slot, said ribs preventing lateral movement of said disk-shaped valve member out of said circumferential slot, and stand-off bosses formed on said lower housing portion on which said disk-shaped valve member rests in the absence of vacuum;
   means for removably attaching said valve mechanism to said hood body adjacent said catch chamber such that said hood mechanism can be readily removed for cleaning; and
   a container communicating with said catch chamber and valve mechanism to receive and hold milk released through said catch chamber outlet.

2. The breastpump of claim 1 wherein said upper valve housing portion is in the form of a split collar, said split collar having a longitudinally extending slot formed therein along part of its length, said upper valve housing portion being removably attached to said collecting chamber by pressing said split collar onto a tubular portion of said catch chamber, said split collar having an interior diameter slightly smaller than the outside diameter of said catch chamber tubular portion so that said split collar is stretched radially outwardly by said catch chamber tubular portion and thereby wedged in placed thereon.

3. The breastpump of claim 2 wherein said valve housing circumferential slot is located immediately below said outlet lip when said valve mechanism is attached to said collecting chamber, said disk-shaped valve member seating against said outlet lip which lip is formed on the end of said catch chamber tubular portion.

4. A breastpump comprising:
   a hood body for placement over a breast, said hood body having a main funnel-shaped portion within which the breast is received and a tubular extension extending downstream from said main funnel portion;
   means for connecting said tubular extension of said hood body with a vacuum line to periodically withdraw air from said hood body in a manner that draws the breast into said main funnel portion and thereby express milk from the breast into said tubular extension;
   a wall formed interiorly of said tubular extension separating said vacuum line connecting means from the breastmilk flow, said wall depending from an upper interior side wall of said tubular extension with said vacuum line connecting means having a connection with said tubular extension above the bottom of said wall, said wall forming a baffle preventing milk from entering said vacuum line;
   a catch chamber for expressed milk connected with said tubular extension, said catch chamber being located downstream from said tubular extension and having an inlet and an outlet;
   a valve mechanism located at said catch chamber outlet, said valve mechanism having a valve member which closes said catch chamber outlet when a vacuum is applied to said hood body and opens said catch chamber outlet when said vacuum is removed;
   means for removably attaching said valve mechanism to said hood body adjacent said catch chamber such that said hood mechanism can be readily removed for cleaning;
   a container communicating with said catch chamber and valve mechanism to receive and hold milk released through said catch chamber outlet; and
   an adjusting piece insertable into said main funnel portion to reduce the interior cross-sectional area of the base of said main funnel portion adjacent said main funnel tubular extension, said funnel-shaped adjusting piece having a funnel portion and a cylindrical extension that is insertable into said main funnel tubular extension, said extension of said adjusting piece being sufficiently long to receive a nipple therein without said nipple extending beyond the downstream end of said adjusting piece extension, distance pieces formed on said extension of said adjusting piece spacing and locating said adjusting piece extension relative to said main funnel tubular extension, a generating angle of an outer surface of said adjusting piece funnel portion corresponding to a generating angle of an inner surface of said main funnel portion, an inner surface of said adjusting piece funnel having a larger generating angle than the generating angle of the outer surface thereof, with a sharp edge being formed about the upstream end of said adjusting piece funnel which sharp edge lies ridgelessly on said inner surface of said main funnel portion.

5. A suction hood for an apparatus for removing mother's milk comprising:
 a main body having the shape of a funnel within which the breast is received;
 an adjusting piece also having the shape of a funnel, said adjusting piece being insertable into said main body funnel to alter at least a portion of the cross-sectional area of said main funnel body at the base of said funnel adjacent a substantially cylindrical extension of said main funnel body, said funnel-shaped adjusting piece having a cylindrical extension insertable into said cylindrical extension of said main funnel body, said cylindrical extension of said adjusting piece being sufficiently long to receive a nipple therein without said nipple extending beyond the downstream end of said adjusting piece extension, distance pieces formed on said extension of said adjusting piece spacing and locating said adjusting piece extension relative to said tubular extension of said main funnel body, a generating angle of an outer surface of said adjusting piece funnel corresponding to a generating angle of the inner surface of said main funnel body, an inner surface of said adjusting piece funnel having a larger generating angle than the generating angle of the outer surface thereof, with a sharp edge being formed about the upstream edge of said adjusting piece funnel which sharp edge lies ridgelessly on said inner surface of said main funnel body.

* * * * *

UNITED STATES PATENT AND TRADEMARK OFFICE
CERTIFICATE OF CORRECTION

PATENT NO. : 4,857,051

DATED : August 15, 1989

INVENTOR(S) : Karl O.A.H. Larsson

It is certified that error appears in the above-identified patent and that said Letters Patent is hereby corrected as shown below:

In column 1, line 31, please delete "pumps" and substitute therefor --pump--.

In column 3, line 2, please delete "chamber" and substitute therefor --container--.

In column 5, line 65, please delete the second occurrence of "the".

In column 6, line 35, please delete "7".

In claim 1, column 9, line 23, please delete "express" and substitute therefor --expresses--.

UNITED STATES PATENT AND TRADEMARK OFFICE
CERTIFICATE OF CORRECTION

PATENT NO. : 4,857,051

DATED : August 15, 1989

INVENTOR(S) : Karl O.A.H. Larsson

It is certified that error appears in the above-identified patent and that said Letters Patent is hereby corrected as shown below:

In claim 4, column 10, line 33, please delete "express" and substitute therefor --expresses--.

Signed and Sealed this

Eighth Day of September, 1992

*Attest:*

DOUGLAS B. COMER

*Attesting Officer*     *Acting Commissioner of Patents and Trademarks*